United States Patent
Bateman

(10) Patent No.: US 8,413,654 B2
(45) Date of Patent: Apr. 9, 2013

(54) METHOD AND APPARATUS FOR RESOLVING UPPER AIRWAY OBSTRUCTION, RESISTANCE OR INSTABILITY

(75) Inventor: Peter Edward Bateman, Bella Vista (AU)

(73) Assignee: Resmed Limited (AU)

( * ) Notice: Subject to any disclaimer, the term of this patent is extended or adjusted under 35 U.S.C. 154(b) by 0 days.

(21) Appl. No.: 11/575,671

(22) PCT Filed: Sep. 28, 2005

(86) PCT No.: PCT/AU2005/001493
§ 371 (c)(1),
(2), (4) Date: Sep. 26, 2008

(87) PCT Pub. No.: WO2006/034549
PCT Pub. Date: Apr. 6, 2006

(65) Prior Publication Data
US 2009/0007914 A1    Jan. 8, 2009

(30) Foreign Application Priority Data
Sep. 28, 2004    (AU) ............................. 2004905584

(51) Int. Cl.
*A61M 16/00*    (2006.01)

(52) U.S. Cl.
USPC ............ 128/204.23; 128/200.24; 128/204.18; 128/204.21

(58) Field of Classification Search ............. 128/200.24, 128/204.18, 204.21, 204.23
See application file for complete search history.

(56) References Cited

U.S. PATENT DOCUMENTS

| | | | |
|---|---|---|---|
| 5,245,995 A | 9/1993 | Sullivan et al. | |
| 5,335,654 A | 8/1994 | Rapoport | |
| 5,551,419 A * | 9/1996 | Froehlich et al. | 128/204.23 |
| 5,598,838 A | 2/1997 | Servidio et al. | |
| 5,645,053 A | 7/1997 | Remmers et al. | |
| 5,704,345 A | 1/1998 | Berthon-Jones | |
| 6,286,508 B1 * | 9/2001 | Remmers et al. | 128/204.18 |
| 6,349,724 B1 * | 2/2002 | Burton et al. | 128/204.18 |
| 6,532,960 B1 * | 3/2003 | Yurko | 128/204.26 |
| 2003/0062045 A1 * | 4/2003 | Woodring et al. | 128/204.18 |
| 2003/0208465 A1 * | 11/2003 | Yurko et al. | 707/1 |

FOREIGN PATENT DOCUMENTS

| | | |
|---|---|---|
| WO | 9812965 | 5/1998 |
| WO | 03075991 | 9/2003 |

* cited by examiner

*Primary Examiner* — Annette Dixon
(74) *Attorney, Agent, or Firm* — Lerner, David, Littenberg, Krumholz & Mentlik, LLP

(57) ABSTRACT

A CPAP apparatus has a variable rise time (iii) from a base level of positive air pressure during expiration (EPAP) to a higher level during inspiration (IPAP). The rise time is adjusted in order to reduce obstruction, resistance or instability in the upper airway.

34 Claims, 3 Drawing Sheets

METHOD AND APPARATUS FOR RESOLVING UPPER AIRWAY OBSTRUCTION, RESISTANCE OR INSTABILITY

CROSS-REFERENCES TO RELATED APPLICATIONS

This application claims the benefit of the filing of Australian Provisional application AU 2004905584 filed Sep. 28, 2004.

BACKGROUND OF THE INVENTION

1. Field of the Invention

The invention relates to non-invasive positive pressure mechanical ventilation, and to methods and apparatus for treatment of sleep disordered breathing.

2. Description of Related Art

The shape of the inspiratory portion of the flow-time curve for a breath is recognised as being indicative of the patency of the upper airway of a person. A normal breath is generally "round". "flattening" of the inspiratory portion of the respiratory flow curve has been recognised as an indication of upper airway instability, resistance or partial obstruction. See FIG. 1. This phenomenon has been used to control a nasal Continuous Positive Airway Pressure (CPAP) device for treating Obstructive Sleep Apnea (OSA). See U.S. Pat. No. 5,704,345 (Michael Berthon-Jones). The contents of this patent are hereby expressly incorporated by cross-reference. The '345 patent describes a method and apparatus for resolving flow limitation by increasing the CPAP pressure provided to the patient until the shape of the flow curve becomes suitably rounded. In some cases, during non-invasive positive pressure mechanical ventilation, increasing the end-expiratory pressure alone may not resolve the upper airway obstruction, resistance or instability. Increasing End Expiratory Pressure (EEP) may lead to a decrease in patient comfort as the result of the increase in both Expiratory Positive Airway Pressure (EPAP) and Inspiratory Positive Airway Pressure.

The present invention is directed towards an alternative method and apparatus for resolving upper airway obstruction, resistance or instability.

SUMMARY OF THE INVENTION

In accordance with one form of the invention there is provided, in a ventilator, a method for reducing or eliminating upper airway obstruction, resistance or instability by adjusting the rise-time of the ventilator.

In a preferred form, obstruction, resistance or instability in the upper airway is reduced by increasing the rise time.

In one preferred form of the invention, the shape of the inspiratory portion of the respiratory airflow is continuously monitored and upon detection of a shape indicative of the presence of upper airway obstruction, resistance or instability ventilator rise-time is adjusted. Preferably, when the shape is flattened, rise time is increased.

In one form, the invention provides a method for operating a CPAP apparatus having a flow generator, a patient interface, an air delivery conduit for delivering air from the flow generator to the patient interface, and a control mechanism that causes air to be delivered through the air delivery conduit at desired pressures at the patient interface, the method comprising the steps of:
  (i) controlling the flow generator to reduce the air flow through the delivery conduit to the patient interface to deliver a lower base level of positive air pressure ("EPAP") in the patient interface during an expiratory portion of the patient's respiratory cycle;
  (ii) controlling the flow generator to increase air flow through the delivery conduit to the patient interface during inhalation so as to maintain the pressure in the patient interface at a higher level ("IPAP") suitable for inhalation, wherein the time for the flow generator to increase the pressure from EPAP to IPAP is a variable rise time; and
  (iii) monitoring the shape of the inspiratory portion of the respiratory airflow and upon detection of a shape indicative of the presence of upper airway obstruction, resistance or instability increasing the rise-time.

A further form of the invention provides a method for reducing or eliminating upper airway obstruction, resistance or instability by use of a CPAP apparatus having a variable rise time from EPAP to IPAP comprising the step of increasing the rise time of the apparatus in response to an indication of an upper airway obstruction, resistance or instability.

A further form of the invention provides a CPAP apparatus having a flow generator, a patient interface, an air delivery conduit for delivering air from the flow generator to the patient interface, and a control mechanism that causes air to be delivered through the air delivery conduit at desired pressures at the patient interface, said apparatus having:
  (i) a lower base level of positive air pressure ("EPAP") in the patient interface during an expiratory portion of the patients respiratory cycle;
  (ii) a higher level ("IPAP") suitable for inhalation, wherein the time for the flow generator to increase the pressure from EPAP to IPAP is a variable rise time; and
  (iii) a controller for monitoring the shape of the inspiratory portion of the respiratory airflow and, upon detection of a shape indicative of the presence of upper airway obstruction, resistance or instability, increasing the rise-time.

A further form of the invention provides a CPAP apparatus having a flow generator, a patient interface, an air delivery conduit for delivering air from the flow generator to the patient interface, and a control mechanism that causes air to be delivered through the air delivery conduit at desired pressures at the patient interface, said apparatus having:
  (i) a lower base level of positive air pressure ("EPAP") in the patient interface during an expiratory portion of the patient's respiratory cycle;
  (ii) a higher level positive air pressure ("IPAP") suitable for inhalation, wherein the time for the flow generator to increase the pressure from EPAP to IPAP is a variable rise time; and
  (iii) a controller for monitoring patient effort for detection of the presence of upper airway obstruction, resistance or instability and upon such detection increasing ventilator rise time.

A further form of the invention provides apparatus for treating sleep disordered breathing comprising:
  a controllable source of breathable gas at positive pressure;
  an air delivery conduit and patient interface adapted to provide gas from said source to the entrance of a patient's airways;
  a flow transducer adapted to provide a flow signal indicative of the respiratory flow of air to the patient's airways;
  a controller programmed to determine the beginning of an inhalation portion of a patient's respiratory cycle from said flow signal and thereupon to increase the pressure of breathable gas from said source from an exhalatory pressure to an inhalatory pressure within an adjustable rise-time; and wherein said controller is further adapted to determine an index of upper airway obstruction from said flow signal and adjust said risetime as a function of said index.

Preferably, when said index of upper airway obstruction indicates partial upper airway obstruction, said controller increases said risetime.

In one aspect of the invention, said index is a shape index, and more preferably a flattening index.

In further aspects of the invention, the index may be a snore index or a hypopnea index.

BRIEF DESCRIPTION OF THE DRAWINGS

Further preferred embodiments of the invention will now be described with reference to the accompanying drawings, in which.

DETAILED DESCRIPTION OF PREFERRED EMBODIMENTS

Figure 1:
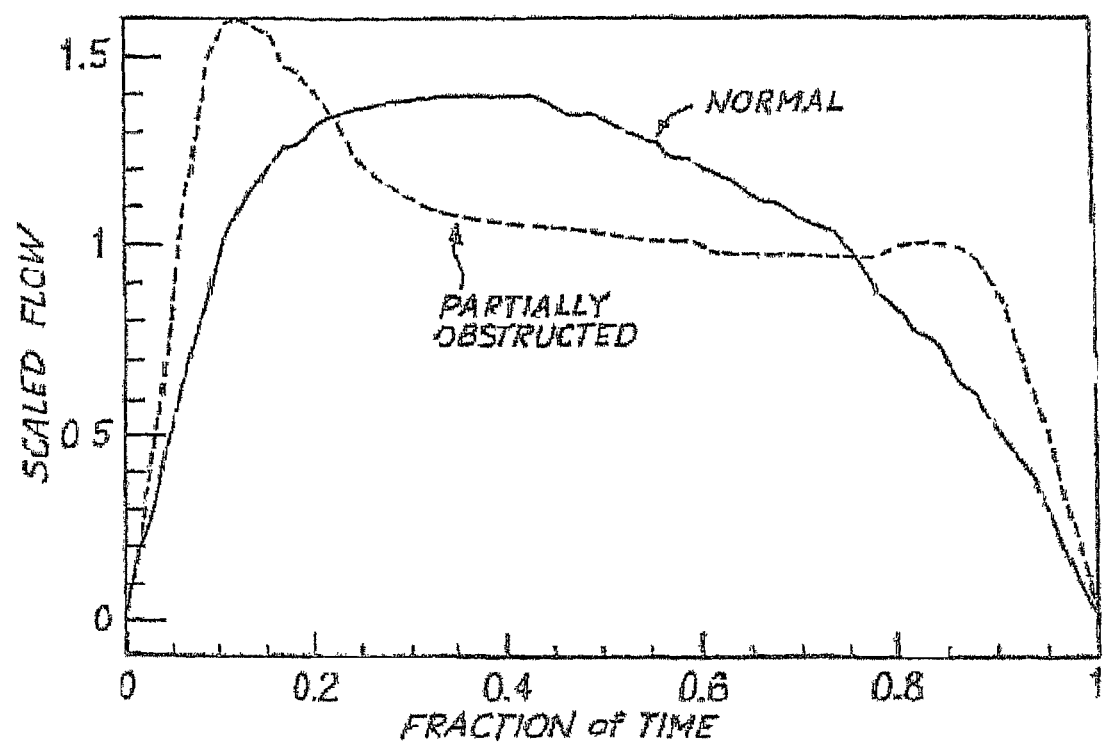
FIG. 1 shows the inspiratory portion of a flow-time curve for a normal breath and a partially obstructed breath (reproduced from U.S. Pat. No. 5,704,345)
Figure 2:
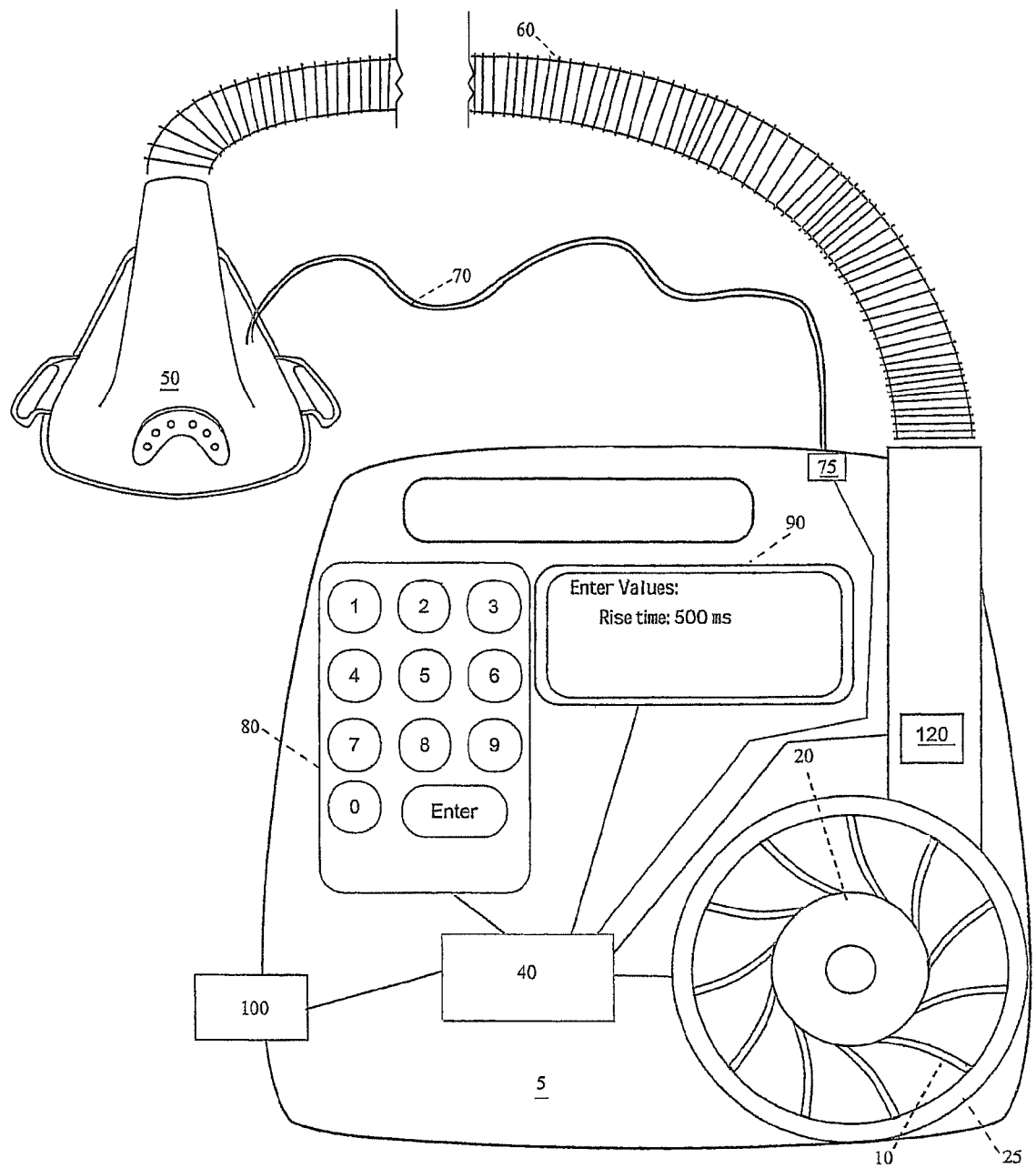
FIG. 2 shows a ventilator, air delivery conduit and patient interface.

FIG. 2 shows apparatus suitable for performing the invention. A device 5 provides a supply of air or breathable gas at positive pressure along an air delivery conduit 60 to a patient interface 50, which in the illustrative form is a mask. A sensing line 70 provides a means for the pressure sensor 75 to measure pressure within the patient interface 50. A volumetric or mass flow sensor 120 measures the flowrate of air along the air delivery conduit 60. An electric motor 20 and its impeller 10 reside in a volute 25 and are under the control of a programmable controller 40. There is a keypad 80 and display 90 allowing various parameters to be adjusted. There is an interface 100 enabling data transfers between the device 5 and other devices, such as a computer or controller (not shown).

A range of pressures of air can be provided depending upon the speed of the blower 20. A base level of positive air pressure (sometimes referred to as the "EEP" or the "EPAP") is delivered during the expiratory portion of the patient's respiratory cycle. Air at a higher pressure is delivered to the patient during the inhalation portion of the breathing cycle (sometimes referred to as the "IPAP"). When inhalation is detected, the blower is accelerated to the speed necessary to deliver IPAP. The time taken for the device to increase the pressure from EPAP to IPAP is termed the "rise time". Device 5 delivers a breath of air to the patient having a pressure-time profile generally resembling a square wave, although a range of pressure-time profiles are known.

Generally, the ventilator is intended to synchronise with patient efforts, that is it delivers a breath when patient effort to breathe can be detected. The ventilator may also be enabled to trigger automatically into IPAP in the case that patient effort is not detected during some operator determined maximum allowable period. A variety of methods may be used in an attempt to monitor patient effort, including pressure and flow sensors, bands around the chest and abdomen and suprasternal notch effort sensors. For example, where inspiratory airflow is taken to be of positive sign and expiratory airflow is taken to be of negative sign, when the airflow crosses zero from negative to positive (or a near zero threshold) the patient is assumed to be attempting to inhale.

Figure 3:
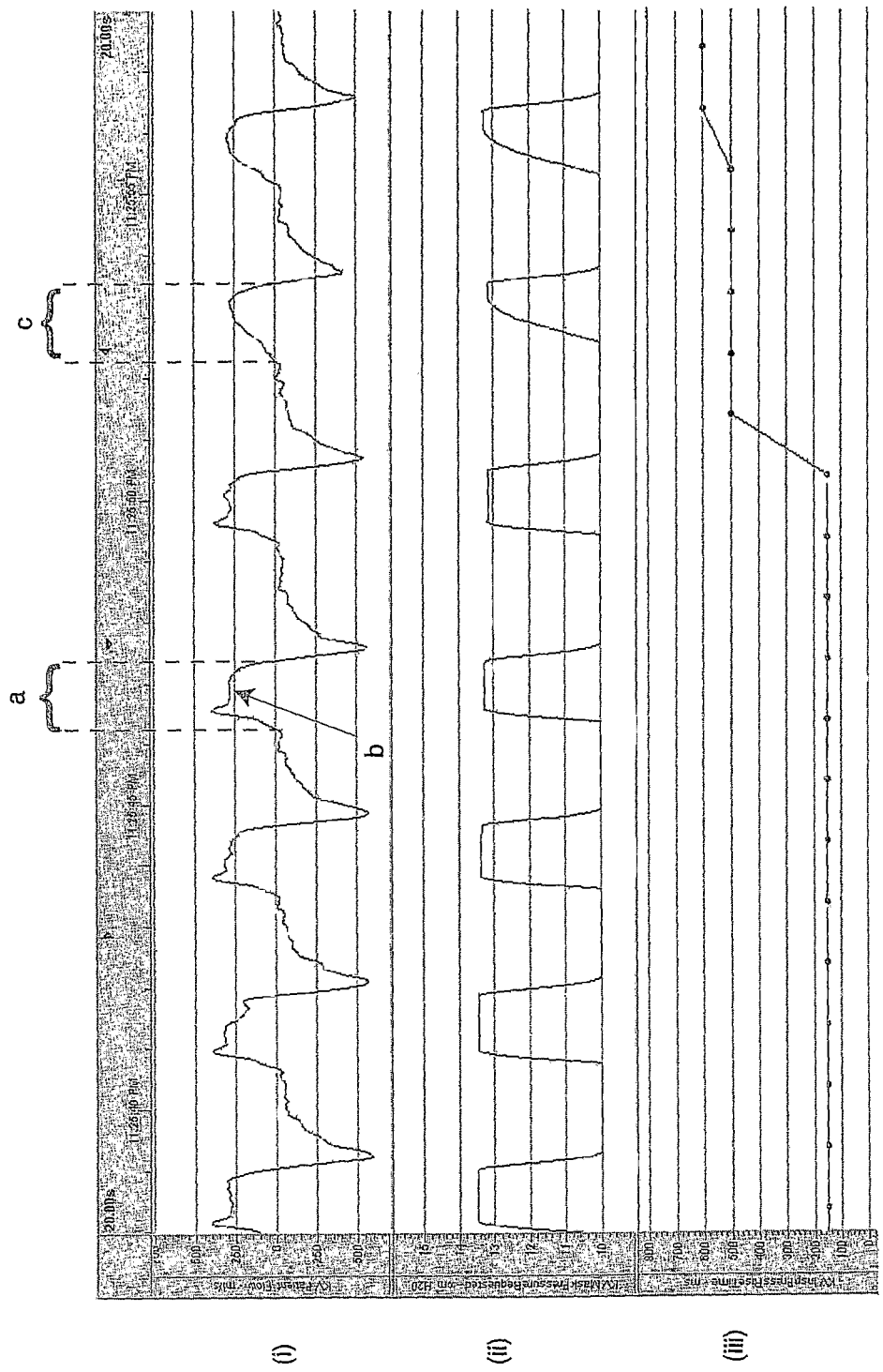
FIG. 3 shows an embodiment of the invention in which flow flattening is resolved.

FIG. 3 shows an embodiment of the invention. There are three traces (i), (ii) & (iii). Trace (i), the upper most trace, shows patient flow (ml/s) with respect to time, where positive pressure indicates inspiration. Region a lies between the broken lines indicating an inspiratory portion. Arrow b points to a flattened inspiratory portion within region a. Region c indicates a rounded inspiratory portion in which flattening has been resolved. Trace (ii), the middle trace, shows mask pressure (cm $H_2O$) with respect to time. Trace (iii), the bottom trace, shows the pressure rise time (ms).

The patient receives a supply of air at about 13.5 cm $H_2O$ during inspiration and approximately 10 cm $H_2O$ during exhalation. For the first five breaths, the rise time is set to approximately 150 ms. The rise time is increased to 500 ms for the sixth breath, and it can be seen by a comparison of regions a and c, that the effect of increasing the rise time has been to resolve the flattening.

Because some patients being ventilated prefer a relatively fast risetime for comfort there may occur a conflict with a clinical desire to provide a relatively slower (ie increased) risetime in order to treat upper airway instability in accordance with the method of the present invention. It is further proposed by the inventor that this conflict may be resolved by providing the increased risetime only during periods of the ventilation treatment when there is detected the onset or occurrence of airway instability. When the patient's airway is stable then the increased risetime may be discontinued and delivery of the ventilation treatment may revert to the faster risetime.

Methods for detecting the onset and occurrence of airway instability are numerous and examples included in the '345 patent, U.S. Pat. No. 5,645,053 (Remmers et al.), U.S. Pat. No. 5,245,995 (Sullivan et al.) and U.S. Pat. No. 5,335,654 (Rapoport). The calculation of indices of upper airway obstruction is discussed more detail in the '345 patent. Any suitable method may be employed to provide information regarding the patient's upper airway patency as an input to the controller of the device 5. Having this information will allow the device 5 to deliver an increased risetime so as to appropriately respond to the patient's upper airway condition when required and to deliver a faster risetime for comfortable ventilation at times when the airway is patent.

By logging the changes in risetime performed by the device 5 a measure may be gained of the number of occurrences and duration of airway instability incident experienced during a treatment session and during an extended course of treatment sessions. This information can serve as an indication as to the patient's condition or to tune ventilator settings.

One of the advantages of the invention is that it can lead to greater comfort for the patient and at the same time increase efficacy and compliance with therapy.

Although the invention has been described with reference to particular embodiments, it is to be understood that these embodiments are merely illustrative of the application of the principles of the invention. Numerous modifications may be made therein and other arrangements may be devised without departing from the spirit and scope of the invention. For example, those skilled in the art recognise that there are other indications of upper airway instability, resistance or obstruction which are not necessarily accompanied by or associated with flow flattening. Furthermore, in another form of the invention, when upper airway instability, resistance or obstruction is detected, the rate of change of pressure from EPAP to IPAP is decreased. In another form, when upper airway instability, resistance or obstruction is detected the time taken to reach 90% of the IPAP pressure is increased.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear. It will further be understood that any reference herein to known prior art does not, unless the contrary indication appears, constitute an admission that such prior art is commonly known by those skilled in the art to which the invention relates.

The invention claimed is:

1. A method for operating a CPAP apparatus having a flow generator, a patient interface, an air delivery conduit for delivering air from the flow generator to the patient interface, and a control mechanism that causes air to be delivered through the air delivery conduit at desired pressures at the patient interface, the method comprising the steps of:
   (i) controlling the flow generator to reduce the air flow through the delivery conduit to the patient interface to deliver a lower base level of positive air pressure ("EPAP") in the patient interface during an expiratory portion of the patient's respiratory cycle;
   (ii) controlling the flow generator to increase air flow through the delivery conduit to the patient interface during inhalation so as to maintain the pressure in the patient interface at a higher level ("IPAP") suitable for inhalation, wherein the time for the flow generator to increase the pressure from EPAP to IPAP is a variable rise time; and
   (iii) monitoring the shape of the inspiratory portion of the respiratory airflow and increasing the rise time upon detection of a shape indicative of the presence of upper airway obstruction, resistance or instability.

2. The method for operating a CPAP apparatus of claim 1, wherein the shape indicative of the presence of upper airway obstruction, resistance or instability is a flattened shape.

3. The method for operating a CPAP apparatus of claim 2, wherein the rise time is increased to a value that resolves the flattening.

4. The method for operating a CPAP apparatus of claim 1, wherein the patient receives a supply of air at about 13.5 cm H2O during inspiration and approximately 10 cm H2O during exhalation.

5. The method for operating a CPAP apparatus of claim 1, wherein the rise time is increased from approximately 150 ms to 500 ms.

6. The method for operating a CPAP apparatus of claim 1, further comprising the step of reducing the rise time when the patient's airway becomes stable.

7. The method for operating a CPAP apparatus of claim 1, further comprising the steps of
   (iv) discontinuing the increased rise time when the patient's airway becomes stable and reverting to a previous faster rise time.

8. The method for operating a CPAP apparatus of claim 1, further comprising the step of logging the changes in rise time performed by the device and providing a measure of the number of occurrences and duration of airway instability incident experienced.

9. A method for reducing or eliminating upper airway obstruction, resistance or instability by use of a CPAP apparatus having a variable rise time from EPAP to IPAP comprising the step of increasing the rise time of the apparatus in response to an indication of an upper airway obstruction, resistance or instability.

10. The method of claim 9 for use in a CPAP apparatus having a flow generator, a patient interface, an air delivery conduit for delivering air from the flow generator to the patient interface, and a control mechanism that causes air to be delivered through the air delivery conduit at desired pressures at the patient interface, the method comprising the steps of:
   (i) controlling the flow generator to reduce the air flow through the delivery conduit to the patient interface to deliver a lower base level of positive air pressure ("EPAP") in the patient interface during an expiratory portion of the patient's respiratory cycle;
   (ii) controlling the flow generator to increase air flow through the delivery conduit to the patient interface during inhalation so as to maintain the pressure in the patient interface at a higher level ("IPAP") suitable for inhalation, wherein the time for the flow generator to increase the pressure from EPAP to IPAP is a variable rise time; and
   (iii) monitoring patient effort for detection of the presence of upper airway obstruction, resistance or instability and upon such detection increasing ventilator rise-time.

11. The method of claim 10, wherein patient effort is monitored by an apparatus selected from the group consisting of pressure and flow sensors, bands around the chest and/or abdomen of the patient and suprasternal notch effort sensors.

12. The method of claim 10, wherein the patient receives a supply of air at about 13.5 cm H2O during inspiration and approximately 10 cm H2O during exhalation.

13. The method of claim 10, wherein the rise time is increased from approximately 150 ms to 500 ms.

14. The method of claim 10, wherein the rise time is increased to a value that resolves the upper airway obstruction, resistance or instability.

15. The method of claim 10, further comprising the step of reducing the rise time when the patient's airway becomes stable.

16. The method of claim 10, further comprising the steps of
   (iv) discontinuing the increased rise time when the patient's airway becomes stable and reverting to a previous faster rise time.

17. The method of claim 10, further comprising the step of logging the changes in rise time performed by the device and providing a measure of the number of occurrences and duration of airway instability incident experienced.

18. A CPAP apparatus having a flow generator, a patient interface, an air delivery conduit for delivering air from the flow generator to the patient interface, and a control mechanism that causes air to be delivered through the air delivery conduit at desired pressures at the patient interface, said apparatus having:
   (i) a lower base level of positive air pressure ("EPAP") in the patient interface during an expiratory portion of the patient's respiratory cycle;
   (ii) a higher level ("IPAP") suitable for inhalation, wherein the time for the flow generator to increase the pressure from EPAP to IPAP is a variable rise time; and
   (iii) a controller for monitoring the shape of the inspiratory portion of the respiratory airflow and, increasing the rise time upon detection of a shape indicative of the presence of upper airway obstruction, resistance or instability.

19. The CPAP apparatus of claim 18, wherein the shape indicative of the presence of upper airway obstruction, resistance or instability is a flattened shape.

20. The CPAP apparatus of claim 19, wherein the rise time is increased to a value that resolves the flattening.

21. The CPAP apparatus of claim 18, wherein the patient receives a supply of air at about 13.5 cm H2O during inspiration and approximately 10 cm H2O during exhalation.

22. The CPAP apparatus of claim 18, wherein the rise time is increased from approximately 150 ms to 500 ms.

23. The CPAP apparatus of claim 18, further comprising the step of reducing the rise time when the patient's airway becomes stable.

24. The CPAP apparatus of claim 18, wherein said controller discontinues the increased rise time when the patient's airway becomes stable and reverts to a previous faster rise time.

25. A CPAP apparatus having a flow generator, a patient interface, an air delivery conduit for delivering air from the flow generator to the patient interface, and a control mechanism that causes air to be delivered through the air delivery conduit at desired pressures at the patient interface, said apparatus having:
  (i) a lower base level of positive air pressure ("EPAP") in the patient interface during an expiratory portion of the patient's respiratory cycle;
  (ii) a higher level positive air pressure ("IPAP") suitable for inhalation, wherein the time for the flow generator to increase the pressure from EPAP to IPAP is a variable rise time; and
  (iii) a controller for monitoring patient effort for detection of the presence of upper airway obstruction, resistance or instability and upon such detection increasing ventilator rise time.

26. Apparatus for treating sleep disordered breathing comprising:
  a controllable source of breathable gas at positive pressure;
  an air delivery conduit and patient interface adapted to provide gas from said source to the entrance of a patient's airways;
  a flow transducer adapted to provide a flow signal indicative of the respiratory flow of air to the patient's airways;
  a controller programmed to determine the beginning of an inhalation portion of a patient's respiratory cycle from said flow signal and thereupon to increase the pressure of breathable gas from said source from an exhalatory pressure to an inhalatory pressure within an adjustable risetime; and
  wherein said controller is further adapted to determine an index of upper airway obstruction from said flow signal and increase said risetime when the index indicates the presence of upper airway obstruction.

27. Apparatus as claimed in claim 26 wherein said controller adjusts said risetime as a function of said index.

28. Apparatus as claimed in claim 26 wherein said index is a shape index.

29. Apparatus as claimed in claim 28 wherein said index is a flattening index.

30. Apparatus as claimed in claim 29 wherein risetime is increased when the flattening index has a value indicative of flattening occurring.

31. Apparatus as claimed in claim 26 wherein said index is a snore index.

32. Apparatus as claimed in claim 26 wherein said index is an hypopnea index.

33. A method for operating a CPAP apparatus having a flow generator, a patient interface, an air delivery conduit for delivering air from the flow generator to the patient interface, and a control mechanism that causes air to be delivered through the air delivery conduit at desired pressures at the patient interface, the method comprising the steps of:
  (i) controlling the flow generator to reduce the air flow through the delivery conduit to the patient interface to deliver a lower base level of positive air pressure ("EPAP") in the patient interface during an expiratory portion of the patient's respiratory cycle;
  (ii) controlling the flow generator to increase air flow through the delivery conduit to the patient interface during inhalation so as to maintain the pressure in the patient interface at a higher level ("IPAP") suitable for inhalation, wherein the time for the flow generator to increase the pressure from EPAP to IPAP is a variable rise time; and
  (iii) increasing the rise time upon detection of the presence of upper airway obstruction, resistance or instability.

34. A CPAP apparatus having a flow generator, a patient interface, an air delivery conduit for delivering air from the flow generator to the patient interface, and a control mechanism that causes air to be delivered through the air delivery conduit at desired pressures at the patient interface, said apparatus having:
  (i) a lower base level of positive air pressure ("EPAP") in the patient interface during an expiratory portion of the patient's respiratory cycle;
  (ii) a higher level positive air pressure ("IPAP") suitable for inhalation, wherein the time for the flow generator to increase the pressure from EPAP to IPAP is a variable rise time; and
  (iii) a controller for increasing the rise time upon detection of the presence of upper airway obstruction, resistance or instability.

* * * * *